(12) United States Patent
Thomas et al.

(10) Patent No.: US 9,791,428 B2
(45) Date of Patent: Oct. 17, 2017

(54) MERCURY SENSOR FOR DETECTING, DIFFERENTIATING, AND MEASURING ORGANIC AND INORGANIC MERCURY COMPOUNDS

(71) Applicant: Chevron U.S.A. Inc., San Ramon, CA (US)

(72) Inventors: David Glynn Thomas, Wembley Downs (AU); Nicholas Paul Langley, Claremont (AU); Nicholas Charles Last, Mount Lawley (AU); Roderick J. Travis, Lafayette, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 162 days.

(21) Appl. No.: 14/303,327

(22) Filed: Jun. 12, 2014

(65) Prior Publication Data
US 2014/0371105 A1 Dec. 18, 2014

Related U.S. Application Data

(60) Provisional application No. 61/834,318, filed on Jun. 12, 2013.

(51) Int. Cl.
*G01N 33/18* (2006.01)
*G01N 33/00* (2006.01)
*G01N 33/28* (2006.01)
*G01N 27/26* (2006.01)
*E21B 43/00* (2006.01)

(52) U.S. Cl.
CPC ...... *G01N 33/1813* (2013.01); *G01N 33/0045* (2013.01); *G01N 33/2835* (2013.01); *B01L 2300/0627* (2013.01); *B01L 2300/0636* (2013.01); *E21B 43/00* (2013.01); *G01N 27/26* (2013.01)

(58) Field of Classification Search
None
See application file for complete search history.

(56) References Cited

U.S. PATENT DOCUMENTS

| | | | | |
|---|---|---|---|---|
| 6,435,007 B1* | 8/2002 | Smith | ...................... | G01N 7/10 73/31.05 |
| 2006/0191319 A1* | 8/2006 | Kurup | .................... | G01N 33/24 73/23.34 |
| 2007/0184557 A1* | 8/2007 | Crudden | ................ | C08G 77/50 436/171 |
| 2012/0021524 A1* | 1/2012 | van Hal | ............... | G01N 33/225 436/81 |
| 2012/0184040 A1* | 7/2012 | Zhang | ................ | G01N 33/1813 436/80 |

* cited by examiner

*Primary Examiner* — Neil N Turk
(74) *Attorney, Agent, or Firm* — Carlos Hanze; Karen R. DiDomenicis; Herbert Smith Freehills LLP

(57) ABSTRACT

The invention relates to a sensor assembly to detect and quantify organic and/or inorganic mercury compounds, including elemental mercury that may be present in gases or liquids, such as natural gas, air, condensates, crude oil, refined petroleum gas or liquids, and water including connate water, condensed water and water containing hydrate inhibitor(s). The sensor assembly includes a housing having a flow channel defined by an inlet, a sensor array, and an outlet. The sensor array is based on the differential sorption properties measured using a surface acoustic wave (SAW) sensor array, a chemiresistor array, or a combination of the two.

11 Claims, 1 Drawing Sheet

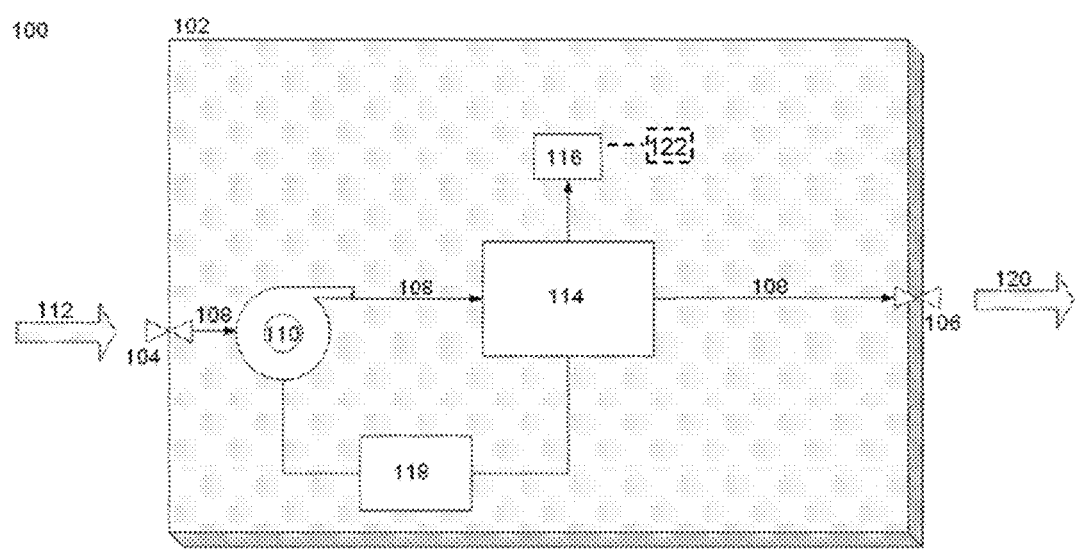

MERCURY SENSOR FOR DETECTING, DIFFERENTIATING, AND MEASURING ORGANIC AND INORGANIC MERCURY COMPOUNDS

FIELD OF THE INVENTION

The invention relates to a sensor assembly for detecting, identifying, and measuring mercury and organic and inorganic mercury compounds, particularly in a gas, crude, or water.

BACKGROUND OF THE INVENTION

Mercury may be naturally occurring in and around natural gas and crude oil fields. As such, conventional methods have been developed to detect the presence of mercury in connection with oil and gas field operations. In accordance with one such conventional method, fluids contained within gas-rich reservoirs are typically characterized initially with Drill Stem Tests (DSTs) and Wireline Formation Tests (WFTs using tools such as the MDTTM or Modular Dynamic Formation Tester). In gas fields that rely on a relatively small number of wells (i.e., less than about 20 wells), WFTs are run at least once per well with the ability to acquire multiple samples. However, other gas fields require thousands of wells to develop a field and, while testing costs per well may be lower, usually by eliminating DSTs and reducing the number and/or scope of WFTs, overall testing costs for comprehensive field-wide fluid characterization may be higher.

Conventional laboratory testing methods for measuring mercury concentrations in natural gas and crude include exposing gas samples to a gold sorbent to capture mercury compounds from the mixture. The mercury compounds are then thermally desorbed and a total mercury concentration is measured using atomic fluorescence spectroscopy. This method is applicable to both organic and elemental forms of mercury with a detection limit down to about 0.001 $\mu g/m^3$. In comparison to such laboratory measurement, the measurement of mercury in natural gas in a reservoir is much more difficult, mainly due to the temperature and pressure conditions that are characteristic of reservoir settings and the difficulty in obtaining and transferring a representative sample from the reservoir for testing above ground. Detection limits under these conditions for total mercury are at best on the order of 1 $\mu g/m^3$ or larger. Due to the changes in conditions, only total mercury measurements are reliable. Specific mercury compounds can be transformed by the process of capturing and moving the sample. Sensor technologies targeted at detecting $Hg^{2+}$ ions in water solutions at ambient temperatures and pressures are reported in the literature. These technologies primarily exploit the optical properties (i.e., fluorescent assays and colorimetric assays) of activated gold nano-particles. Aside from the focus of these sensors on the detection of mercury ions in water solutions, the practical lower detection limits of such methods is generally not better than 20 ppb, which is consider to be too high to be useful in characterising mercury compounds in natural gas or crude oil.

As such, a need exists for a sensor that is capable of detecting and speciating organic and inorganic mercury compounds in gas, crude, or water to a practical quantification limit of 1 $\mu g/m^3$ or lower.

SUMMARY OF THE INVENTION

The invention relates to a sensor assembly to detect and quantify organic and/or inorganic mercury compounds, including elemental mercury, in gas or liquids, such as natural gas, natural gas condensates, air, crude oil, refined petroleum gas or liquids, and water including connate water, condensed water and water containing hydrate inhibitor.

The sensor assembly includes a number of components including a sensor housing having a flow channel defined by an inlet, a sensor array, and an outlet. The sensor housing will also include a pump to draw a sample through the inlet, over the sensor array, and to expel the sample through the outlet.

The sensor array is based on the differential sorption properties measured using a surface acoustic wave (SAW) sensor array, a chemiresistor array, or a combination of the two. To the Applicants' knowledge, in the oil and gas industry chemiresistor and acoustic wave sensor arrays have not previously been used in situ to monitor and report the detection and concentrations of inorganic and organic mercury compounds.

Accordingly, in one aspect of the invention there is provided a sensor assembly for detecting and measuring a concentration of a mercury analytes in a fluid stream selected from the group consisting of mercury, and organic and inorganic mercury compounds; the assembly including: a housing for containing elements of the sensor assembly; a sensor array including a chemiresistor sensor array, an acoustics wave sensor array, or a combination thereof; an inlet channel through which a sample is drawn into the housing and into contact with the sensor array; an outlet channel through which the sample is expelled from the housing; and a sampler located within the housing for drawing the fluid sample into the housing via the inlet channel and expelling the sample via the outlet channel; wherein the sensor array is configured to detect and measure the concentration of the mercury analytes in the fluid sample and produce an electrical output signal indicative of the type and concentration of the mercury analytes detected.

An advantage of the invention is that is that it provides an integrated sensor assembly that can be placed at a sampling location and left to run independently. Due to this arrangement, the sensor assembly has a small footprint in comparison with currently available downhole instrumentation. Typically, the volumetric size of the sensor is about 12 U.S. fl oz.

The sensor assembly includes within the housing the essential components required for the sensor assembly to function and therefore is easy to install and operate. This provides flexibility in the installation of the sensor assembly, for example the sensor assembly can be rapidly deployed temporarily in a downhole without having to install ancillary equipment to accompany the sensor. Similarly, the sensor may be deployed semi-permanently or permanently, for example on a wellhead platform or processing plant.

In an embodiment the sensor assembly will be used to detect, speciate, and measure a concentration of a mercury analytes in crude oil and natural gas reservoirs. Accordingly, in this embodiment the sensor assembly is configured to operate at temperatures of from about 60° C. to about 300° C. and under pressures of from about 2000 psi to about 8000 psi.

Another advantage of the invention resides in the use of chemiresistor and acoustic wave sensor arrays which allow the detection and speciation of multiple mercury analytes in a gas at a quantification limit of about 1 $\mu g/m^3$ and/or mercury analytes in a liquid at a quantification limit of about 1 $\mu g/L$. The use of these sensors also permits continuous or near continuous measurements to be made, and provides for a rapid response time after exposure to a fluid sample of the order of seconds.

In an embodiment the sensor array includes a plurality of sensors each having a thiol layer to interact with the mercury analytes. Preferably, the plurality of sensors includes at least two sensors having different thiol layers with different interaction strengths with the mercury analytes. More preferably, the plurality of sensors includes at least three sensors having different thiol layers with different interaction strengths with the mercury analytes, such that the plurality of sensors includes: a first sensor having a first thiol layer, the first thiol layer having a strong interaction strength with a first analyte, a second sensor having a second thiol layer, the second thiol layer having a weak interaction strength with the first analyte, and a third sensor having a third thiol layer, the third thiol layer having an interaction strength with the first analyte that is between the strong interaction strength and the weak interaction strength.

In an embodiment the sensor assembly further includes a power source located within the housing for powering the sampler and/or sensing component.

In an embodiment the sensor assembly further includes a processor located within the housing, the processor configured to: receive the electrical output signal from the sensor array; and apply principal component analysis to determine the type and concentration of the mercury analytes detected. Alternatively, the sensor assembly further includes a processor located within the housing, the processor being configured to store as data the signal indicative of the type and concentration of the mercury analytes detected. This data may either be raw data from the sensor array, or the processor may be configured to analyse the data to determine the type and concentration of the mercury analytes detected. The data may then be downloaded on retrieval of the sensor assembly, or the data may be transmitted to a location remote from the sensor assembly.

In an embodiment the sensor assembly further includes a transmitter located within the housing for communicating to a remote location either the raw data from the sensor array or the analysed data including the type and concentration of the mercury analytes detected.

In an embodiment the sensor array is a sensor array selected from the group consisting of a surface acoustic wave sensor array, a chemiresistor sensor array, or a combination of both.

In an embodiment the sensor array includes both a chemiresistor sensor array and an acoustics wave sensor array. Preferably the sensor array consists of both a chemiresistor sensor array and an acoustics wave sensor array.

The sensor housing may also include membrane interfaces and/or filters.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 1 is a block diagram of an embodiment of the invention.

DETAILED DESCRIPTION OF THE EMBODIMENTS

The invention relates to a sensor assembly unit for the detection and quantification of mercury analytes, such as organic and/or inorganic mercury compounds, including elemental mercury, in gas or liquids, such as natural gas, natural gas condensates, air, crude oil, refined petroleum gas or liquids, and water including connate water, condensed water and water containing hydrate inhibitor.

The identification of elemental mercury is particularly important. Elemental mercury refers to mercury in its metallic form, and is intended to encompass mixtures of mercury with other metals or compounds such as amalgams of mercury, as well as the various isotopes of mercury.

Organic mercury (or organomercury) compounds may include dialkyl mercury compounds (e.g. dimethylmercury, diethylmercury, diphenyl mercury), mercury carboxylates (e.g. mercuric acetate), alkyl mercury compounds (such as methylmercury and ethylmercury compounds), alkyl mercury halides.

Inorganic mercury compounds may include both Hg(I) and Hg(II) compounds such as mercury(I) halides, mercury(II) halides, mercury(I) nitrate, mercury(II) nitrate, mercury(I) oxide, mercury(II) oxide, mercury(I) sulfate, mercury(II) sulfate, mercury(II) cyanide, mercury(II) thiocyanante, mercury nitride, mercury selenide, mercury sulfide, mercury telluride.

The mercury compound may be a complex such as having a formula Hg-L or Hg-$L_2$, where L represents a ligand.

The sensor assembly is a module that has a housing that that incorporates the necessary components such that the sensor assembly has a small footprint and can quickly and easily be installed in a desired location, such as in an oil or gas reservoir, a downhole, a wellhead platform, or in a processing plant. It has been found that a sensor assembly including a sensor array chosen from a surface acoustic wave sensor, a chemiresistor, or both, is particularly well suited to the detection of mercury analytes.

Surface acoustic wave sensors are a class of microelectromechanical systems that rely on modulation of surface waves to detect, identify, and quantify mercury analytes in a fluid sample. Surface acoustic wave sensors use the piezoelectric effect in their operation. Surface acoustic wave sensors use an input interdigitated transducer (IDT) to convert an electrical signal into an acoustic wave. The transmitter IDT has a thin surface layer of a molecule such as an oligomer, polymer, or other organic molecule applied thereto. A known electrical signal is applied to the transmitter IDT to produce a known acoustic wave. A sorption interaction between an analyte and the surface layer can alters the transmitted acoustic wave. A receiver IDT converts the transmitted acoustic wave back into an electrical signal. The input electrical signal and the output electrical signal are then compared. Any significant difference will likely be the result of the interaction of the analyte and the surface layer on the transmitter IDT. Different analytes have different effects on the transmitted acoustic wave. An array of sensors can be constructed using a wide variety of organic molecules as the thin surface layer, such as different polymers, that differ in their responses to various analytes.

Chemiresistor sensors are made from conductive nanoparticles coated in a monolayer of a molecule such as an oligomer, polymer, or other organic molecule. The response of the sensor to a chemical is measured as a change in the resistance of the sensor. For a chemiresistor sensor, upon exposure to an analyte the analyte diffuses into the molecule and the molecule swells, which causes the dispersed conductive nanoparticles to move further apart from each other, causing the resistance of the sensor to increase. Different analytes have different effects on the resistance of the sensor. An array of polymer composite sensors can be constructed from a wide variety of organic molecules, such as different polymers, that differ in their responses to various analytes.

The sensor arrays of the invention may include a plurality of surface acoustic wave sensors, a plurality of chemiresistor sensors, or a combination of both surface acoustic wave sensors and chemiresistor sensors. At least some of the individual sensors in the array will be coated with different thiol molecules than other sensors. When the sensor array is exposed to a fluid (whether gas or liquid) containing either a single mercury analyte or a mixture of mercury analytes, each individual coated sensor device responds in a different manner due to a different interaction with the analyte (on account of the sensors possessing different thiol layers). Certain thiol molecules will interact strongly with certain mercury compounds, while other thiol molecules will interact strongly with other mercury compounds present in a fluid sample.

Given the various responses of either a surface acoustic wave or chemiresistor sensor array to various analytes, samples can be classified, identified and quantified by using statistical methods, such as principle component analysis (PCA). This allows the types and concentrations of various mercury analytes in a sample to be determined.

Thiol molecules have been found to be particularly useful in the detection, identification, and quantification of mercury analytes, including both organic and inorganic mercury compounds. For this reason, the acoustic wave sensor arrays and chemiresistor sensor arrays of the present invention include a sensor layer that has been functionalised with thiol molecules. By selecting thiol molecules with a varied range of responses, it is possible to have an array of sensors that can detect, identify, and quantify a multitude of different mercury analytes.

It has been found that thiol layers that are formed from a thiol selected from the group consisting of substituted or unsubstituted: alkanethiol, alkenethiol, alkynethiol, arylthiol, heteroalkanethiol, heteroalkenethiol, heteroalkynethiol, or heteroarylthiol, are particularly useful in both acoustic wave sensor arrays and chemiresistor sensor arrays for the detection of a mercury analyte.

Additionally, thiol molecules that contain between 2 and 30 carbon atoms, preferably 4 to 20 carbon atoms, and even more preferably between 5 and 15 carbon atoms, are found to be particularly advantageous. Similarly, thiol molecules with a chain length of between 2 and 30 atoms, preferably 4 and 20 atoms, and even more preferably 5 and 15 atoms are found to be particularly advantageous.

Furthermore, particularly useful thiol molecules include those that are terminated at one end with a thiol, and at another end with a functional group selected from the group consisting of: carboxyl, carboxylate, hydroxyl, aldehyde, carbonyl, haloformyl, ester, peroxy, methoxy, amine, amide, aldimine, azide, cyanate, isocyanate, nitrile, isonotrile, nitrosooxy, nitro, nitroso, fluoride, chloride, bromide, iodide, thiol, sulfide, disulfide, sulfinyl, sulfonyl, sulfino, sulfo, thiocyanate, isothiocyanate, carbonothioyl, phosphino, phosphono, phosphate; or a fused or unfused substituted or unsubstituted 3 to 6 membered heterocyclic or aryl ring. The thiol portion of the molecule bonds with the metal surface of the surface acoustic wave sensor array or form a monolayer around the gold nanoparticles of the chemiresistor sensor array. Another end of the thiol molecule, having a functional group selected from above, is free to interact with the mercury analytes.

FIG. 1 provides an illustration of an embodiment of a sensor assembly 100. The sensor assembly 100 includes a sensor housing 102 having an inlet 104 and an outlet 106 and a flow path 108 between the inlet 104 and the outlet 106. A sampler (which in this case is a pump) 110 is mounted within the sensor housing 102. The pump 110 draws a fluid sample containing mercury analytes 112 through the inlet 104 and inside the sensor housing 102. The outlet of the pump 110 feeds the fluid sample to a sensor array 114. The analyte in the fluid sample 112 interacts with the surface of the sensors in the sensor array 114 to produce an output signal that is indicative of the type and concentration of mercury analytes in the fluid sample 112. This output signal is then received by a processor 116 which records the signal and then applies an algorithm, such as PCA, to convert the signal into data that represents the types and concentrations of mercury analytes detected. The processor then logs the data. The analysed fluid sample 120 is then exits from the sensor and is expelled from the sensor housing 102 through the outlet 106. A power supply 118, such as a battery, is used to supply power to the various components of the sensor assembly 100 that require power, such as the pump 110, the sensor array 114, and the processor 116. The sensor assembly 100 can then be retrieved and the data can be downloaded and analysed using if required.

As previously discussed, the sensor array 114 may be a surface acoustic wave sensor array, a chemiresistor sensor array, or a combination of both. By 'array' it is meant that the sensor array includes a plurality of sensors. In this particular embodiment the sensor array 114 includes a plurality of sensors, each of the sensors being functionalised with a thiol layer, some of the sensors having different thiol layers to other sensors.

While FIG. 1 relates to an embodiment in which a liquid fluid sample is analysed, it is intended that the sensor assembly can also be used to detect, identify, and quantify the presence of mercury analytes in a gas stream. In this situation the pump 110 may be replaced with another device to drive a gaseous fluid through the system such as a fan or blower.

In another alternative arrangement, the sensor assembly may be situated in a fluid stream (whether gas or liquid) and the sampler is an intake structure that feeds a fluid sample to the sensor. In this situation, the fluid pressure of the fluid stream is sufficient to drive the fluid sample through the inlet and the intake structure, over the sensor array, and then out through the outlet.

In another alternative arrangement, the processor 118 communicates with a transmitter 122 to transmit the information.

In a further alternative embodiment the sensor assembly includes a viewable display. In this alternative embodiment, the processor is configured to analyse the data from the sensor array to provide as an output the types and concentrations of mercury analytes present in the sample, and to transmit this information to the display to display the information.

In yet a further alternative embodiment other analytical tools can be used to interpret the raw data from the sensor array.

In an embodiment, the output signal from the sensor array may be processed by a computer, or a control system with a computer, and displayed as an output on a user interface. A notification device may be provided, which generates a notification that includes information relating to the type and concentrations of the various organic analytes in the sample. The control system may, for example, be a SCADA system, which provides system control and data acquisition. Where such instrumentation is provided, the data generated by the sensor assembly may be displayed locally in the vicinity of the sensor assembly. Alternatively or in addition, the data may be provided to the sensor assembly for display on a user interface and storage in memory.

In an embodiment the sensor assembly includes at least one computational device, which may be a microprocessor, a microcontroller, a programmable logical device or other suitable device. Instructions and data to control operation of the sensor assembly may be stored in a memory which is in data communication with, or forms part of, the computational device. Typically, the sensor assembly includes both volatile and non-volatile memory and may include more than one of each type of memory. The instructions and data for controlling operation of the sensor assembly may be stored on a computer readable medium from which they are loaded into the memory. Instructions and data may be conveyed to and from the sensor assembly by means of a data signal in a transmission channel. Examples of such transmission channels include network connections, the internet or an intranet and wireless communication channels.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for in-situ detection, speciation, and measurement of a concentration of at least one mercury analyte in a liquid in an oil and gas reservoir, a downhole, or a wellhead platform, comprising:
   a. providing a sensor assembly comprising:
      i. a housing for containing elements of the sensor assembly;
      ii. a sensor array within the housing comprising a surface acoustic wave sensor array, a chemiresistor sensor array, or a combination of both;
      iii. an inlet channel through which the liquid is drawn into the housing and into contact with the sensor array;
      iv. an outlet channel through which the liquid is expelled from the housing;
      v. a sampler within the housing for drawing the liquid into the housing via the inlet channel and expelling the liquid via the outlet channel; and
      vi. a processor located within the housing;
      wherein the sensor array includes a plurality of sensors each having a thiol layer comprising a thiol selected from the group consisting of substituted or unsubstituted: alkanethiol, alkenethiol, alkynethiol, arylthiol, heteroalkanethiol, heteroalkenethiol, heteroalkynethiol, and heteroarylthiol; wherein the thiol is terminated at one end with a functional group to interact with the at least one mercury analyte;
   b. placing the sensor assembly in a location selected from the group consisting of the oil and gas reservoir, the downhole, and the wellhead platform wherein the location has a temperature from about 60° C. to about 300° C. and a pressure of from about 2000 psi to about 8000 psi;
   c. drawing in by the sampler the liquid through the inlet channel to the sensor array of the sensor assembly such that the at least one mercury analyte in the liquid interacts with the functional group of the thiol layers by sorption to a degree depending on the type and concentration of the at least one mercury analyte in the liquid;
   d. continuously producing an electrical output signal indicative of the type and concentration of the at least one mercury analyte sorbed based on the interaction of the at least one mercury analyte in the liquid with the functional group of the thiol layers in step (c);
   e. in the processor, receiving the electrical output signal from the sensor array; and
   f. in the processor, applying principal component analysis to the electrical output signal to determine the type and concentration of the at least one mercury analyte sorbed.

2. A method for in-situ detection, speciation, and measurement of a concentration of at least one mercury analyte in a liquid in an oil and gas reservoir, a downhole, or a wellhead platform, comprising:
   a. providing a sensor assembly comprising:
      i. a housing for containing elements of the sensor assembly;
      ii. a sensor array within the housing comprising a surface acoustic wave sensor array, a chemiresistor sensor array, or a combination of both;
      iii. an inlet channel through which the liquid is drawn into the housing and into contact with the sensor array;
      iv. an outlet channel through which the liquid is expelled from the housing;
      v. a sampler within the housing for drawing the liquid into the housing via the inlet channel and expelling the liquid via the outlet channel;
      vi. a processor located within the housing; and
      vii. a transmitter in communication with the processor;
      wherein the sensor array includes a plurality of sensors each having a thiol layer comprising a thiol selected from the group consisting of substituted or unsubstituted: alkanethiol, alkenethiol, alkynethiol, arylthiol, heteroalkanethiol, heteroalkenethiol, heteroalkynethiol, and heteroarylthiol; wherein the thiol is terminated at one end with a functional group to interact with the at least one mercury analyte;
   b. placing the sensor assembly in a location selected from the group consisting of the oil and gas reservoir, the downhole, and the wellhead platform wherein the location has a temperature from about 60° C. to about 300° C. and a pressure of from about 2000 psi to about 8000 psi; and
   c. drawing in by the sampler the liquid through the inlet channel to the sensor array of the sensor assembly such that the at least one mercury analyte in the liquid interacts with the functional group of the thiol layers onto the functional group by sorption to a degree depending on the type and concentration of the at least one mercury analyte in the liquid;
   d. continuously producing an electrical output signal indicative of the type and concentration of the at least one mercury analyte sorbed based on the interaction of the at least one mercury analyte in the liquid with the functional group of the thiol layers in step (c);
   e. in the processor, storing as data the electrical output signal from the sensor array;
   f. transmitting the stored data to a remote processor at a remote location;
   f. receiving the stored data in the remote processor at the remote location; and
   g. in the remote processor, applying principal component analysis to the electrical output signal to determine the type and concentration of the at least one mercury analyte sorbed.

3. The method of claim 1 or 2, wherein the plurality of sensors includes at least three sensors having different thiol layers with different interaction strengths with the at least one mercury analyte, such that the plurality of sensors includes:
  a first sensor having a first thiol layer, the first thiol layer having a strong interaction strength with a first of the at least one mercury analyte, a second sensor having a second thiol layer, the second thiol layer having a weak interaction strength with the first of the at least one mercury analyte, and a third sensor having a third thiol layer, the third thiol layer having an interaction strength with the first of the at least one mercury analyte that is between the strong interaction strength and the weak interaction strength.

4. The method of claim 1 or 2, wherein the functional group is selected from the group consisting of: carboxyl, carboxylate, hydroxyl, aldehyde, carbonyl, haloformyl, ester, peroxy, methoxy, amine, amide, aldimine, azide, cyanate, isocyanate, nitrile, isonotrile, nitrosooxy, nitro, nitroso, fluoride, chloride, bromide, iodide, thiol, sulfide, disulfide, sulfinyl, sulfonyl, sulfino, sulfo, thiocyanate, isothiocyanate, carbonothioyl, phosphino, phosphono, phosphate; or a fused or unfused substituted or unsubstituted 3 to 6 membered heterocyclic or aryl ring.

5. The method of claim 1 or 2, further including a power source located within the housing for powering the sampler and/or sensing component.

6. The method of claim 1 or 2, wherein the sensor array determines the concentration of the at least one mercury analyte at a quantification limit of about 1 µg/L.

7. The method of claim 1 or 2, wherein the thiol contains between 2 and 20 carbon atoms.

8. The method of claim 1 or 2, wherein the thiol contains between 5 and 15 carbon atoms.

9. The method of claim 1 or 2, wherein the plurality of sensors includes at least two sensors having different thiol layers with different interaction strengths with the at least one mercury analyte.

10. The method of claim 1 wherein the sensor assembly further comprises a transmitter in communication with the processor for transmitting the determined type and concentration of the at least one mercury analyte sorbed to a remote location.

11. The method of claim 1 or 2, wherein the sensor assembly is placed in a liquid stream in the oil and gas reservoir, the downhole, or the wellhead platform wherein the liquid stream has sufficient fluid pressure to drive the liquid through the inlet channel to the sensor array and out through the outlet channel.

* * * * *